July 15, 1969 R. BAERMAN Plant Pat. 2,903
GLADIOLUS PLANT
Filed Nov. 24, 1967
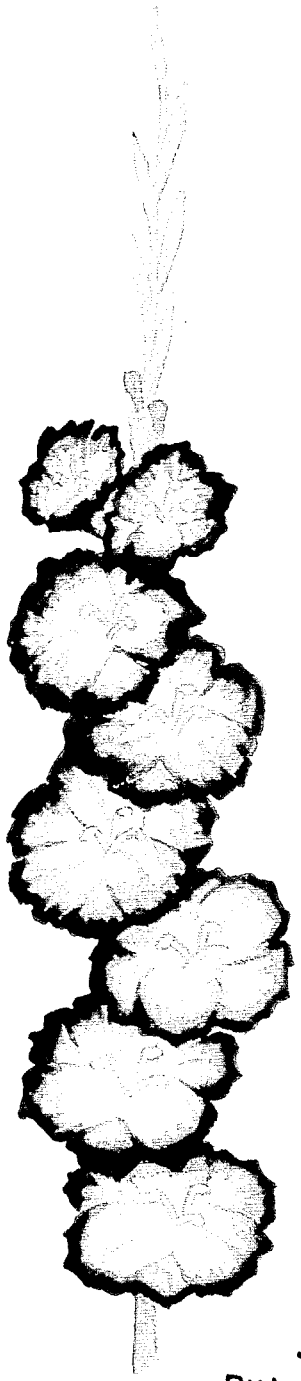
INVENTOR
Ralph Baerman
By: Lamont Johnston
ATTORNEY United States Patent Office Plant Pat. 2,903
Patented July 15, 1969

2,903
GLADIOLUS PLANT

Ralph Baerman, Salem, Oreg., assignor to Selected Glads, Inc., New Albany, Ind., a corporation of Tennessee Filed Nov. 24, 1967, Ser. No. 685,717
Int. Cl. A01h *5/02*
U.S. Cl. Plt.—85 1 Claim My invention relates to a new and improved variety of gladiolus plant and is notable particularly for its small size, unique blossom color contract, and ability to perform well in all parts of the United States.

To the best of my knowledge, this variety is the result of a cross between my miniature, Blue Midget (unpatented) and one of my other smaller blue unnamed seedlings (all unpatented), of which I used several as pollen parents on Blue Midget. The pollination was done by me in my garden in Salem, Oreg.

This new variety has been asexually reproduced by me in Oregon, by natural increase from cormels through several generations and its characteristics have proven to be permanently fixed.

The illustration, made a part of this application, shows a single bloom spike, reduced in size, and is as nearly true to color and floret form as it is possible to depict.

In the following detailed description, color plate references are to "The Horticultural Colour Chart" by the British Colour Council. Where there are other references to color, the ordinary dictionary meanings of color terms are intended.

The plant

Growth: Healthy; grows to 45 inches in height overall. Good propagator.

Blooming: Blooms in 75 days in the North from mature corms.

Stems: Diameter of stem is ⅓ inch. Color of the stem above corm is white.

Foliage: Bright green, upright. Leaves are 1¼ inches across. Foliage excluding the flower spike, is 33 inches tall.

Disease resistance: Excellent resistance to prevailing gladiolus diseases.

Corms: Round, medium-large, well-husked, ivory colored.

The flower

Spike: Flowerhead is 18 inches high, with 16 to 18 buds of which 7 to 8 are open at one time.

Bud: Opening buds are 2 inches long.

Flower: Florets are formally placed on a neat, uncrowded spike. Diameter of blooms is 2¼ inches. Form is round and very lightly waved. Keeping qualities are excellent.

Petals: Average substance. No fragrance. Color is a uniform medium-light violet blue, blending to a small contrasting creamy white throat. Tips of petals are Spectrum Violet 735/1, shading to 735/2 to 735/3 and then to white in center of floret. Throat is creamy white.

Reproductive organs: Stamens ivory, tinted violet at edges. Pistil—ivory.

Comparisons

My new variety resembles Blue Midget (unpatented) but differs as follows:

Color is notably bluer and brighter and white throat is more contrasty. Floret form is neater and more formal. Propagation is superior.

Having thus disclosed my invention, I claim:

1. The new and distinct variety of gladiolus plant, substantially as shown and described herein, characterized by its small size, blossom color contrast, distinctiveness and ability to perform well in all parts of the United States.

No references cited.

ROBERT E. BAGWILL, Primary Examiner